(12) United States Patent
Plasse

(10) Patent No.: US 6,703,418 B2
(45) Date of Patent: *Mar. 9, 2004

(54) APPETITE STIMULATION AND INDUCTION OF WEIGHT GAIN IN PATIENTS SUFFERING FROM SYMPTOMATIC HIV INFECTION

(75) Inventor: Terry Plasse, New York, NY (US)

(73) Assignee: Unimed Pharmaceuticals, Inc.

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 07/893,554

(22) Filed: Jun. 3, 1992

(65) Prior Publication Data

US 2003/0100602 A1 May 29, 2003

Related U.S. Application Data

(63) Continuation of application No. 07/661,514, filed on Feb. 26, 1991, now abandoned.

(51) Int. Cl.$^7$ ............................................. A61K 31/35
(52) U.S. Cl. ..................................................... 514/454
(58) Field of Search ........................................ 514/454

(56) References Cited

PUBLICATIONS

Vaupel, D. B. et al, Pharmacol Biochem Behav 17(3): 539–545 (1982).*
Noyes, R, et al, Comp Psychiatry 17(5): 641–646 (1976).*
Gorter, R., Management of *Anorexia–cachexia* Associated with Cancer and HIV Infection, Supplement Oncology, vol. 5, No. 9, p. 13–17, (1991).
Friedman H., Klien T., Specter S., Pross S., Newton, C., Blanchard DK., Widen R., Drugs of Abuse and Virus Susceptibility, Psychological Neuropsychiatric and Aspects of Aids, Raven Press, New York, (1998), p. 125–137.
Noe SN., Nyland SB, Ugen K., Friedman H., Klein TW., Cannabinoid Receptor Agonists Enhance Sycytia Formation in MT–2 Cells Infected With Cell Free HIV–1 mn,Drugs of Abuse, Immunomodulation, and AIDS,p. 223–229, (1998).

Srivastava MD., Srivastava BIS., Brouhard B., Tetrahydrocannabinol and Cannabidiol Alter Cytokine Production by Human Immune Cells, Immunopharmacology 40 p. 179–185 (1998).
Harkins T., Herriott KB., Medical Management of Acquired Immune Deficiency Syndrome Patients: a Review, J. of The American Optometric Association, vol. 63, No. 1, p. 35–42, (1/92).
Anderson, P.O. and G.G. McGuire, "Deltra–9–tetrahydrocannabinol as an Antiemetic," Am. J. Hosp. Pharm., 38: 639–46 (1981).
MacGregor, R.R., "Alcohol and Drugs as Co–Factors for AIDS," Adv. Alcohol Subst. Abuse, 7(2):47–71 (1987).
Pillai, R.M., and R.R. Watson, "In vitro Immunotoxicology and Immunopharmacology: Studies on Drugs of Abuse," Toxicology Letters, 53: 269–283 (1990).
Pillai et al., "AIDS, Drugs of Abuse and the Immune System: A Complex Immunotoxicological Network," Arch. Toxicol., 65: 609–617 (1991).
Pross et al., "Differential Suppression of T–Cell Subpopulations By THC (Delta–9–Tetrahydrocannabinol)," Int. J. Immunopharmac., 12(5): 539–544 (1990).
Schwartz C.J., "AIDS and Marijuana Use," Hosp Community Psychiatry., 38(5):530–1 (1987).
Specter et al., "Combined Immunosuppressive Activities of Delta–9–Tetrahydrocannabinol and Murine Retrovirus," Adv. Exp. Med. Biol., 288:135–141 (1991).
Specter et al., "Delta–9–Tetrahydrocannabinol Augments Murine Retroviral Induced Immunosuppression and Infection," Int. J. Immunopharmac., 13(4): 411–417 (1991).
Tidall et al., "The Sydney AIDS Project: Development of Acquired Immunodeficiency Syndrome in a Group of HIV Seropositive Homosexual Men," Aust. NZ J. Med, 18: 8–15 (1988).

* cited by examiner

*Primary Examiner*—Russell Travers
(74) *Attorney, Agent, or Firm*—Mayer, Brown, Rowe & Maw, LLP; Joseph A. Mahoney; Amanda T. Barry

(57) ABSTRACT

Patients with symptomatic HIV infection, including AIDS and ARC are treated to increase appetite and to cause a reduction in loss of weight. The delta-9-tetrahydrocannabinol may be administered orally, in capsules, or in tablets, or by injection, suppository, intranasal, transdermal, inhalant or sublingual administration.

17 Claims, No Drawings

APPETITE STIMULATION AND INDUCTION OF WEIGHT GAIN IN PATIENTS SUFFERING FROM SYMPTOMATIC HIV INFECTION

This is a continuation of application(s) Ser. No. 07/661,514 filed on Feb. 26, 1991, now abandoned.

BACKGROUND OF THE INVENTION

Among the many problems endured by patients suffering from symptomatic HIV infection, which includes inter alia AIDS (Acquired Immune Deficiency Syndrome) and ARC (AIDS Related Complex), are loss of appetite with consequent loss of weight. This loss of appetite and loss of weight further debilitates the patients and increases the many problems associated with the HIV infection.

The compound delta-9-tetrahydrocannabinol, which is the active ingredient in marijuana and which was produced chemically as described in U.S. Pat. No. 3,668,224, has been used as an antiemetic to relieve nausea and vomiting in patients receiving cancer chemotherapy.

A number of cancer investigators have used delta-9-tetrahydrocannabinol to attempt to increase appetite and modify weight loss in cancer patients. For example, in a randomized double-blind crossover study employing oral delta-9-tetrahydrocannabinol and prochlorperazine, 50% of the subjects on delta-9-tetrahydrocannabinol reported an increased food intake while only 29% had a similar response on the prochlorperazine.[1] In another study of similar design and using the same medications, patients on delta-9-tetrahydrocannabinol reported feeling more hungry than patients on prochlorperazine.[2] Results suggestive of an appetite stimulating effect were also noted by Ekert, et al.[3] in groups of children and adolescents 6–19 years of age administered delta-9-tetrahydrocannabinol, prochlorperazine or metaclopramide in crossover design studies.

[1] Sallan, S E; Cronin, C; Zelen, M; and Zinberg, N E (Sidney Farber Cancer Institute, Boston, Mass.): Antiemetics in patients receiving chemotherapy for cancer. A randomized comparison of delta-9-tetrahydrocannabinol and prochlorperazine. N. Engl. J. Med. 301:135–138 (Jan. 17) 1980, No. 3.
[2] Ungerleider, J T; Andrysiak, T; Fairbanks, L; Gooodnight, J; Sarna, G; and Jamison, K. (UCLA Center for the Health Sciences, Los Angeles, Calif.): Cannabis and cancer chemotherapy. A comparison of oral delta-9-THC and prochlorperazine. Cancer 50:636–645 (Aug. 15) 1982, No. 4.
[3] Ekert, H; Waters, K D; Jurk, I H; Mobilia, J; and Loughnan, P. (Royal Children's Hospital, Melbourne, Australia): Amerlioration of cancer chemotherapy-induced nausea and vomiting by delta-9-tetrahydrocannabinol. Med. J. Aust. 2:657–659 (Dec. 15) 1979.

In a double blind study, Regelson, et al.[4] observed that advanced cancer patients on chemotherapy receiving delta-9-tetrahydrocannabinol maintained their weight better than those not receiving the delta-9-tetrahydrocannabinol.

[4] Regelson W, Butter J R; Schultz J; Kirk T; Peek L; Green M L; Delta-9-tetrahydrocannabinol, (delta-9-THC) as an effective antidepressant and appetite-stimulating agent in advanced cancer patients. The pharmacology of marihuana, (Braude M C & Szara S eds) Raven Press, N.Y. (1976; pp. 763–766.

In an open study, Wadleigh, et al.[5] observed appetite increases and a lessening of the rate of weight loss in cancer patients.

[5] Wadleigh, R; Spaulding, M; Lembersky, B; Zimmer, M; Shepard, K; Plasse, T: Dronabinol enhancement of appetite in cancer patients. Proceedings, 1990 American Society of Clinical Mycology Meeting.

SUMMARY OF THE INVENTION

It is accordingly a primary object of the present invention to provide for the treatment of patients suffering from symptomatic HIV infection so as to improve the appetite and induce weight gain in such patients.

Other objects and advantages of the present invention will be apparent from a further reading of the specification and of the appended claims.

With the above and other objects in view, the present invention mainly comprises the administration to a patient suffering from symptomatic HIV infection of an appetite stimulating effective amount of delta-9-tetrahydrocannabinol.

The delta-9-tetrahydrocannabinol is preferably administered orally as dronabinol (delta-9-tetrahydrocannabinol in sesame oil-containing capsules). Administration is also possible to achieve the effects of the present invention when the delta-9-tetrahydrocannabinol is in the form of tablets, suppositories, intranasal administration, transdermal administration, inhalants and sublingual administration, as well as administration by injection.

Side effects, such as nausea and CNS effects, may vary with the dosage of the delta-9-tetrahydrocannabinol. It is a further object of this invention to optimize the dosage regimen so as to minimize such side effects.

DESCRIPTION OF THE PREFERRED EMBODIMENTS

The following is given to further illustrate the present invention. The scope of the invention is not, however, meant to be limited to the specific details thereof.

EXAMPLE I

Soft gelatin capsules were filled with delta-9-tetrahydrocannabinol in sesame oil (dronabinol). Capsules were filled with 2.5 mg delta-9-tetrahydrocannabinol per capsule or 5 mg delta-9-tetrahydrocannabinol per capsule.

Ten symptomatic HIV patients were treated with delta-9-tetrahydrocannabinol. The patients studied were all homosexual males; one had a history of intravenous drug abuse as well. The infectious complications which they had represent the spectrum of those usually seen in a symptomatic HIV-infected population.

Most of the patients had received or were on antiviral therapy, primarily zidovudine (azidothymidine). Two had previously received and one was receiving megesterol acetate as well. Patients received delta-9-tetrahydrocannabinol as dronabinol (delta-9-tetrahydrocannabinol in sesame oil in soft gelatin capsules), usually at a dose of 2.5 mg, for one to five months. Treatment continued for most of the patients at the time of this analysis. The dose varied. The patients were instructed to take medication up to four times daily as needed; many took it somewhat less often.

Initially, patients were losing a median of 0.93 kg/mo. On therapy, they gained 0.54 kg/mo. The median difference on versus pre-therapy was 1.92 kg/mo. Seven patients gained weight while two others had a decrease in weight loss. This result was unexpected as previous studies in cancer patients showed that while weight loss lessened, patients rarely gained weight.

EXAMPLE II

In a prospective, dose-ranging study, 23 patients with symptomatic HIV infection were treated with dronabinol at a dose of 2.5 mg twice daily to 5.0 mg three times daily. Of these, 13 completed approximately one month on therapy. Of those completing one month on therapy, seven gained weight.

At a dose which appears optimal, seven of eight patients completed one month treatment. At that dose, most patients did not experience side effects. Most of those patients who did experience side effects found them tolerable. Confirming the unexpected results of Example I, five of the seven patients gained weight. The median rate of weight loss prior to therapy was 1.62 kg/mo; on therapy, the median weight gain was 1.56 kg/mo. The median improvement in the rate of weight change was 3.06 kg/mo, or approximately 1.5 lbs/wk.

It thus appears that delta-9-tetrahydrocannabinol can provide a significant tool in the treatment of patients with symptomatic HIV infection by improving appetite and reducing weight loss.

While the invention has been illustrated with respect to specific dosages, it is apparent that variations and modifications can be made without departing from the spirit or scope of the invention.

What is claimed is:

1. A method of treating a patient with symptomatic HIV infection to stimulate weight gain in the patient, which comprises administering to the patient a pharmaceutical composition comprising delta-9-tetrahydrocannabinol in an amount sufficient to cause an increase in weight of the patient.

2. The method according to claim 1 wherein said administration is orally.

3. The method according to claim 1 wherein said delta-9-tetrahydrocannabinol is administered in the form of capsules containing delta-9-tetrahydrocannabinol in sesame oil.

4. The method of claim 1, wherein the composition is in a dosage form selected from the group consisting of intranasal solution or suspension, inhalant solution or suspension, parenteral solution or suspension, transdermal patch, transdermal gel, and transdermal cream.

5. The method of claim 1, wherein the composition is administered in a dosage form selected from the group consisting of tablet, capsule, inhalant, injectable, transdermal, sublingual, and suppository.

6. The method of claim 5, wherein the dosage form is an inhalant.

7. The method of claim 6, wherein the inhalant is administered orally.

8. The method of claim 5, wherein the capsule is a soft gelatin capsule.

9. The method of claim 1, wherein the composition is administered to a patient on antiviral therapy.

10. The method of claim 1, wherein the delta-9-tetrahydrocannabinol is dronabinol.

11. The method of claim 1, wherein the composition is administered to the patient by a route selected from the group consisting of oral, intranasal, inhalation, injection, transdermal, and sublingual.

12. The method of claim 11, wherein the inhalation comprises oral inhalation.

13. The method of claim 1, wherein the composition is administered in an amount from about 2.5 mg delta-9-tetrahydrocannabinol to about 20 mg delta-9-tetrahydrocannabinol per day.

14. The method of claim 13, wherein the composition is administered in an amount of about 2.5 mg delta-9-tetrahydrocannabinol per day.

15. The method of claim 13, wherein the composition is administered once daily.

16. The method of claim 13, wherein the composition is administered twice daily.

17. The method of claim 13, wherein the composition is administered in a single dose.

* * * * *